United States Patent
Wagner et al.

(10) Patent No.: US 8,524,274 B2
(45) Date of Patent: Sep. 3, 2013

(54) LIPOSOMAL COMPOSITION COMPRISING AN ACTIVE INGREDIENT FOR RELAXING SMOOTH MUSCLE, THE PRODUCTION OF THIS COMPOSITION AND THE THERAPEUTIC USE THEREOF

(75) Inventors: Andreas Wagner, Baden (AT); Karola Vorauer-Uhl, Vienna (AT); Hermann Katinger, Vienna (AT)

(73) Assignee: Polymun Scientific Immunbiologische Forschung GmbH, Vienna (AT)

( * ) Notice: Subject to any disclaimer, the term of this patent is extended or adjusted under 35 U.S.C. 154(b) by 923 days.

(21) Appl. No.: 11/577,488

(22) PCT Filed: Oct. 14, 2005

(86) PCT No.: PCT/EP2005/011054
§ 371 (c)(1),
(2), (4) Date: Aug. 28, 2009

(87) PCT Pub. No.: WO2006/042701
PCT Pub. Date: Apr. 27, 2006

(65) Prior Publication Data
US 2009/0324698 A1    Dec. 31, 2009

(30) Foreign Application Priority Data
Oct. 18, 2004 (EP) .................................. 04024753

(51) Int. Cl.
*A61K 9/127* (2006.01)
*A61K 31/00* (2006.01)
*A61K 31/44* (2006.01)
*A01N 43/42* (2006.01)

(52) U.S. Cl.
USPC ...................... 424/450; 514/210.21; 514/289

(58) Field of Classification Search
None
See application file for complete search history.

(56) References Cited

U.S. PATENT DOCUMENTS

| | | | |
|---|---|---|---|
| 4,448,765 A * | 5/1984 | Ash et al. ...................... | 424/450 |
| 4,937,078 A | 6/1990 | Mezei et al. | |
| 6,762,202 B2 * | 7/2004 | Marek et al. .................. | 514/515 |
| 6,833,139 B1 * | 12/2004 | Lemko et al. ................. | 424/450 |
| 7,265,091 B2 * | 9/2007 | Lue et al. ....................... | 514/8.1 |
| 7,901,708 B2 * | 3/2011 | MacLachlan et al. ........ | 424/450 |
| 2004/0014761 A1 | 1/2004 | Place et al. | |

FOREIGN PATENT DOCUMENTS

| | | |
|---|---|---|
| EP | 0967214 A1 | 12/1999 |
| JP | 02-196713 A | 8/1990 |
| WO | 94/28902 A1 | 12/1994 |
| WO | 96/14083 A1 | 5/1996 |
| WO | 99/21558 A2 | 5/1999 |
| WO | 02/36257 A1 | 5/2002 |
| WO | 03032947 A2 | 4/2003 |
| WO | 03/059320 A1 | 7/2003 |
| WO | 2004/037262 A2 | 5/2004 |
| WO | 2004/047800 A2 | 6/2004 |
| WO | 2004/047801 A2 | 6/2004 |

OTHER PUBLICATIONS

Langry, et al. (1999) "Sildenafil: A Review of its Use in Erectile Dysfunction", Drugs, 57(6): 967-89.*
Foldvari, et al. (1998) "Liposome Encapsulated Prostaglandin E1 in Erectile Dysfunction: Correlation Between in vitro Delivery through Foreskin and Efficacy in Patients", Urology, 52(5): 838-43.*
Junuzovic, et al. (2004) "Therapy of erectile dysfunction—public health aspects", Med. Arh., 58(1 Suppl. 1): 66-8 (Abstract Only).*
Anne S. Ulrich, "Biophysical Aspects of Using Liposomes as Delivery Vehicles", Bioscience Reports, Apr. 2002, 22(2):129-150.

* cited by examiner

*Primary Examiner* — Robert M Kelly
(74) *Attorney, Agent, or Firm* — Rothwell, Figg, Ernst & Manbeck, P.C.

(57) ABSTRACT

The invention relates to a pharmaceutical composition made from an active ingredient included in liposomes for topical application, whereby the liposomes have an aqueous medium in the interior thereof and contain at least one active ingredient therein which exerts a direct or indirect relaxing effect on smooth musculature and is preferably selected from the group of prostaglandins, adenylate cyclases, cAMP, AMP, ATP, NO-synthetases, nitrogen monoxide (NO), NO compounds, nitrates, guanylate cyclases, cGMP, GMP, GTP and phosphodiesterases, in particular, Sildenafil. The invention further relates to a method for production of said composition, optionally, in sterile form and the use of the liposomes supporting the active ingredient in various galenic forms for external application in the genital region, for prophylaxis and/or therapy of sexual disorders in men or women and/or for increase of sexual sensitivity.

14 Claims, 1 Drawing Sheet

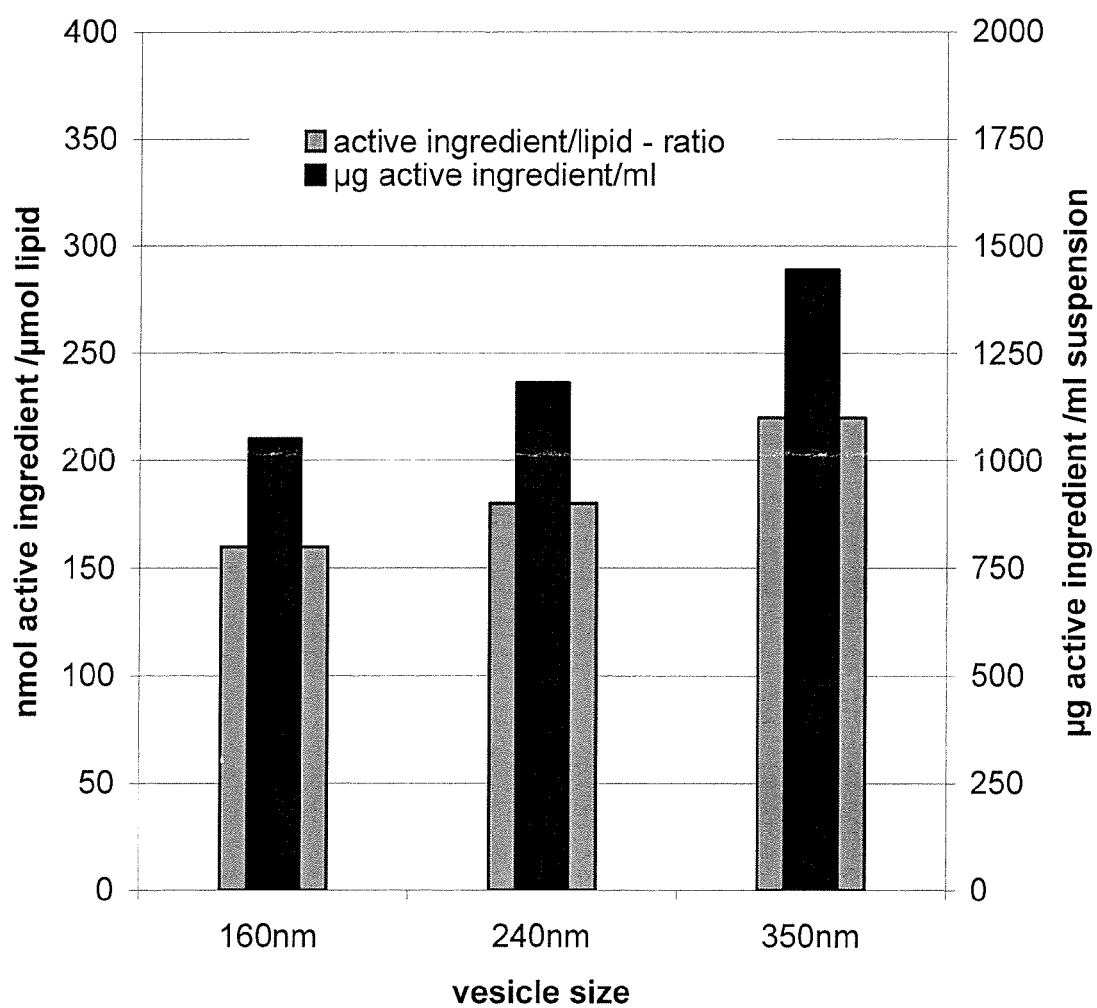

LIPOSOMAL COMPOSITION COMPRISING AN ACTIVE INGREDIENT FOR RELAXING SMOOTH MUSCLE, THE PRODUCTION OF THIS COMPOSITION AND THE THERAPEUTIC USE THEREOF This application is a National Phase of International Application Ser. No. PCT/EP2005/011054, filed 14 Oct. 2005.

FIELD OF THE INVENTION

The present invention relates to pharmaceutical compositions based on topically applicable active ingredients in liposomes, which enhance the blood flow through tissues, in particular in the genital area, and to the production of such compositions and the use thereof.

BACKGROUND OF THE INVENTION

Liposomes are known to be agents for the controlled release of pharmaceutical active ingredients (cf. for example overview by Ulrich, Biosci Rep. 2002; 22(2):129-50 or WO 96/14083 for SOD in liposomes). The formulation of local anaesthetics in topically applied liposomes is also known to the person skilled in the art; for example, U.S. Pat. No. 4,937,078 describes liposomes which comprise customary sodium channel blockers, such as tetracaine, lidocaine, etc. Other known chemical compounds are those which promote blood flow through tissues and have become known especially through their use for eliminating erectile dysfunction and impotence (cf. for example WO 94/28902 and EP 0967214 A1).

SUMMARY OF THE INVENTION

While the known active ingredient preparations based on pyrazolopyrimidones and pyrazolopyrimidinones are present as formulations which can be administered either orally or intranasally, the object of the present invention is to provide a composition for effective topical use of such substances, preferably directly in the genital area, in particular a formulation which permits an overall low but at the same time sufficiently high local dose of these active ingredients in the area of the female or male sex organs.

This object is achieved, according to the invention, by the provision of a liposomal system for topical, in particular transdermal and/or transmucosal, administration of active ingredients which relax the smooth muscles, especially those of the blood-supplying vessels in the sex organs. Such an effect can be triggered, for example, by an induced secretion of calcium ions.

DETAILED DESCRIPTION OF THE INVENTION

In a first embodiment, the invention relates to a formulation in which the active ingredient, preferably from the group consisting of the prostaglandins, adenylate cyclases, cAMP, AMP, ATP, NO synthetases, nitric oxide (NO), NO compounds, nitrates, guanylate cyclases, cGMP, GMP, GTP and phosphodiesterases, in particular sildenafil, tadalafil and vardenafil, is included in liposomes and/or is present bound to liposomes.

The liposomal formulation according to the invention achieves not only a temporary active ingredient depot in the surrounding tissue from which substance is continuously released but also better bioavailability and a longer half-life in comparison with systemic use.

The relaxing effect on the smooth muscle cells results in enhanced blood flow through the externally treated tissues, for example of the sex organs, and consequently in increased sensitivity and sensibility in sexual activities.

Active ingredients or active substances in the context of the present invention are in particular those substances which intervene in the cAMP or cGMP circulation and give rise to increased CA ion secretion. These include, for example, substances such as papaverine and phentolamine which stimulate the cAMP pathway; nitric oxide (NO) which performs an important transmitter function and activates a guanylate cyclase which in turn forms cGMP; NO donors; nitroglycerin; minoxidil; L-arginine; linsidomine (produced in the body by NO synthetase by conversion of arginine to citrulline); molsidomine; phosphodiesterase inhibitors, such as, for example, sildenafil or sildenafil citrate, which intervenes in the cGMP pathway, a PDE5 receptor being involved; prostaglandins, such as, for example, alprostadil (PGE-1), dinoprostone (PGE-2), which intervene in the cAMP circulation.

Where sildenafil is mentioned below, tadalafil, vardenafil and the acidic salts thereof, e.g. sildenafil citrate and vardenafil HCl·$3H_2O$ (vardenafil hydrochloride trihydrate), are also meant thereby, unless evident otherwise from the respective context.

The scalable method disclosed in WO 02/36257 for active ingredient encapsulation has proved to be particular advantageous for the production and loading of the liposomes with active ingredient, owing to its high efficiency in combination with extremely gentle conditions of the method. This method is typically used to produce unilamellar liposomes which have a lipid double-layer membrane and whose extremely good skin penetrability has already been recognized and proven in earlier work. Other methods disclosed in the prior art for the production and loading of liposomes can, however, also be used.

A maximum loading density can be achieved by active loading of the liposomes with active ingredients. This process can be divided into two main categories: loading of the membrane and loading of the intraliposomal aqueous phase. Active ingredients which comprise protonatable groups, for example amino groups, can be included in liposomes by $H^+$ gradient-controlled loading and then retained there in the protonated state. For this type of active loading, the most important feature is the liposome membrane/liposome medium partition coefficient. It was found that the octanol/buffer partition coefficient provides a good indication of the transmembrane diffusion of a substance and is therefore relevant for the loading with active ingredient or for the release profile.

On the basis of this theoretical model, liposomes having different lipid compositions, preferably comprising long-chain phospholipids and having low cholesterol concentrations, were produced in a suitable loading buffer, preferably in an ammonium sulphate or citric acid/sodium carbonate buffer. After the production of the liposomes in ammonium sulphate or citrate buffer, the surrounding medium is modified, i.e. exchanged or diluted, optionally neutralized or made alkaline, and an $H^+$ gradient is produced thereby between the intraliposomal buffer and the extraliposomal medium. After addition of an active ingredient to the extraliposomal medium, the active ingredient migrates into the liposomes owing to this $H^+$ gradient, is protonated there and remains stable in the liposomes.

On application of this technique, the extent of loading or the loading capacity is determined primarily by the ratio of $H^+$ concentrations inside and outside the liposomes. In the experiments carried out, it was possible to achieve, with active ingredient/lipid ratios in the range of 200-400 nmol of active ingredient per μmol of lipid, values similar to those known from the literature relating to actively loaded liposomes. An increase in the active ingredient concentration in the loading medium led to no increase in the loading capacity.

The active loading described above is a three-stage process consisting of vesicle formation, addition of active ingredient and alkalinization. A further object of the invention was therefore to establish a one-stage production method which could be realized with the use of the crossflow module disclosed in WO 02/36257. For this purpose, the active ingredient was dissolved in an $H^+$-rich, aqueous phase, e.g. ammonium sulphate solution or citric acid solution, and included in liposomes by means of the crossflow injection technique and immediately thereafter the remaining external (=extraliposomal), aqueous phase was diluted with a dilution buffer (e.g. 5% glucose solution in the ammonium sulphate system or citric acid/sodium carbonate pH 9.0-9.5 in the citrate system). It was found that the quality of the active ingredient-laden liposomes can be improved simply by variation, in particular by reduction, of the cholesterol content in the vesicle membrane, especially with regard to the skin penetrability thereof.

Where required or desired, the loading capacity can be further increased by raising the average liposome size from about 150-200 nm (as generally used in the experiments described herein) to 300-500 nm. In addition, the efficiency of the method, i.e. the amount of liposomally included active ingredient per ml of suspension, can also be further increased by increasing the lipid concentration either during production or during the subsequent filtration of the vesicles.

If sildenafil is used as the active ingredient, the ammonium sulphate/glucose solution system is preferable for active loading, since sildenafil is only poorly soluble or not soluble at all in citrate buffer. $NH_3$, which is present in a reversible equilibrium with ammonium sulphate in the intraliposomal aqueous medium, attempts to migrate out through the liposome membrane and to leave behind an $H^+$. Sildenafil migrates in the opposite direction into the liposome, takes up the hydrogen ion $H^+$, becomes more hydrophilic thereby and therefore remains in the membrane. In this way, sildenafil can be efficiently loaded into liposomes. This applies in a similar manner also to the sildenafil alternatives tadalafil and vardenafil.

For determining the best liposome formulation in relation to membrane flexibility and the associated skin penetration properties, various liposome suspensions having different lipid compositions were prepared and tested. Phospholipids, optionally in combination with cholesterol, were primarily used. However, it is within the scope of the invention to replace or to supplement phospholipids with other lipids, for example with glycolipids, cerebrosides, sulphatides or galactosides. Typical members of the lipids which can be used are, for example, phosphatidylethanolamine, phosphatidylcholine, phosphatidylserine, phosphatidylinositol, phosphatidylglycerol, cardiolipin, sphingomyelins, plasmalogens, glyceroglycolipids, ceramide, glycophingolipids and neutral glycophingolipids.

One possibility for improving the membrane fluidity important for transdermal applications is to reduce the phase transition of the liposomal double layer membrane, which is determined chiefly by the length of the acyl chains of the phospholipids, the amount of cholesterol and the saturation of the phospholipids. For this reason, in one embodiment of the production method, DPPC, a phospholipid having an acyl chain length of 16 carbon atoms, was replaced by DMPC (chain length of 14 carbon atoms), which reduces the melting point TM from about 45° C. to 31° C.

A second possibility for reducing the membrane rigidity and increasing the fluidity is to reduce the proportion of cholesterol in the membrane. Starting from a DPPC:cholesterol ratio of 55:45 mol % (as described in the literature for liposome loading), the amount of cholesterol was gradually reduced to 38 or 30%, based on the total lipid content. A slight decrease in the active ingredient loading was found in comparison with the results with higher cholesterol contents. However, these liposomes showed improved skin penetration properties and remained stable without significant active ingredient loss even in a long-term test over weeks.

In contrast to discoveries in earlier work, it was also possible to produce stable cholesterol-free liposomes and successfully load them with active ingredient so that, according to the invention, the cholesterol content is in a range of 0-50 mol % based on the total lipid content.

A third possibility for making liposomal membranes more flexible is to replace the fully saturated DPPC or DMPC lipids with hen's egg phosphatidylcholine (E-PC), a natural lipid mixture with unsaturated phospholipids. In addition to stability problems with the use of these natural lipids, it was also necessary to produce the liposomes under a nitrogen atmosphere. Nevertheless, these vesicles gave neither good results with respect to the vesicle size and homogeneity nor improvements in the skin penetration properties.

It is within the scope of the present invention also to use alternative, functionally equivalent systems known to the person skilled in the art for the formation of an $H^+$ gradient. In this context, "functionally equivalent" is to be understood as meaning the ability to form an $H^+$ gradient across the lipid double layer membrane of the liposomes and not to destroy the membrane integrity in the process, so that included, in particular protonated, active ingredient remains stable—in the context of the stability criteria disclosed herein—in the liposomes.

For use of a liposomal sildenafil composition as a therapeutic agent to be used topically, the liposomes are preferably mixed into a hydrogel, which is easier to apply to the skin than a pure suspension. However, it is within the scope of the present invention also to produce other galenical formulations for the sildenafil liposomes and to apply them topically, in particular formulations in the form of solutions, lotions, emulsions, tinctures, sprays, ointments or creams. The person skilled in the art in this area is familiar with further possibilities as well as the required, pharmaceutically admissible accompanying substances and additives for the production of the various galenical formulations.

In earlier experiments, for example, Carbopol 981NF (from Noveon), a hydrogel which can be used in very low concentrations, proved useful. It is admissible for pharmaceutical use, relatively cheap to acquire and available in large amounts.

BRIEF DESCRIPTION OF THE FIGURE

FIG. 1 shows a graph of the included amounts of sildenafil in DPPC/cholesterol liposomes as a function of the vesicle size.

For better illustration, the invention is explained further with reference to the following examples.

EXAMPLE 1

Production of Sildenafil Liposomes

The liposomes are preferably produced by the known crossflow method (WO 02/36257) using an aqueous phase suitable for the desired active ingredient, optionally at least a part of the active ingredient being initially taken in this aqueous phase and being included in the interior of the liposomes in the course of the liposome formation. The subsequent dilution of the liposome suspension by means of neutral or alkaline dilution buffer, which preferably also contains active ingredient, produces an $H^+$ gradient between the inside and outside of the liposomes, which both rapidly and efficiently transports further protonatable active ingredient from the dilution buffer into the liposomes and retains the active ingredient already included in the course of the liposome formation.

Alternatively, it is also possible to choose a method in which, in a first step, buffer-filled liposomes without active ingredient are produced and the active ingredient is loaded into the liposomes actively via an $H^+$ gradient, as described above, only after the liposome production. This procedure makes it possible to check the quality of the liposome suspension before loading with active ingredient.

Both techniques are very reproducible and permit the inclusion of any desired active ingredients in liposomes. They can also be carried out under extremely mild process conditions and make it possible completely to dispense with the use of possibly harmful solvents and in particular with the use of shear forces for vesicle formation.

In addition, it is possible with this crossflow method to provide all reagents in sterile or germ-free form and to carry out the liposome production and loading under aseptic conditions so that a sterile or germ-free product in the form of liposomes laden with active ingredient finally results.

Liposome production (according to WO 02/36257) in detail:

The lipid mixture is dissolved in 96% ethanol and, depending on the choice of lipid or lipid composition, at a temperature in the range of 25 to 60° C., for example at a temperature at 50 to 55° C. in the case of DPPC liposomes, with stirring. The buffer solutions, too, are preferably thermostatted at the same temperature, for example 55° C. While the polar, aqueous phase (buffer) is pumped through the crossflow module by means of a pump, e.g. a peristaltic pump, the ethanol/lipid solution is simultaneously injected into the polar phase under a pressure which can be pre-selected as desired.

Initial tests have shown that, depending on the active ingredient used, different buffer systems also exhibit different suitability for the production of the $H^+$ gradient which permits the active loading. Thus, for example with the use of sildenafil citrate as active ingredient, a buffer system of citric acid (intraliposomal) and an equimolar, neutral or slightly basic buffer, such as, for example, citric acid/sodium carbonate pH 7.5-8.0 (extraliposomal), has proved to be disadvantageous since sildenafil citrate is insoluble or scarcely soluble in buffer systems of this type. On the other hand, sildenafil citrate dissolves very readily in water, and it is for this reason that the active loading with ammonium sulphate gradients is preferred for this active ingredient.

By means of this method, liposomes are therefore preferably formed in the presence of an ammonium sulphate buffer (preferably 125 mmol). After the vesicle formulation, the aqueous phase which has remained outside the liposomes, in this case the ammonium sulphate solution, is modified, for example diluted by means of dilution buffer or replaced with a 5% glucose solution by means of diafiltration, with the result that small amphiphilic molecules, such as sildenafil, can be loaded into the liposomes and protonated there, while $NH_3$ escapes from the liposomes in the opposite direction.

a) Two-Stage Variant:

External loading of liposomes with sildenafil by means of $H^+$ gradient. The best inclusion rates were achieved under the following conditions. The lipids (molar DPPC:cholesterol ratio=55:45; in total 13 to 15 µmol per ml of aqueous phase) were dissolved in ethanol and this solution was injected into 125 mM ammonium sulphate solution. After spontaneous vesicle formation, the remaining, external ammonium sulphate solution was replaced by a 5% glucose solution and sildenafil citrate was added. In this way, an $H^+$ gradient formed between the inside and outside of the lipid vesicles. pH values below 2.5 are less suitable owing to resultant hydrolysis problems, and pH values greater than 5.5 are also not preferred, owing to the increasingly flat $H^+$ gradient. An aqueous 125 mM ammonium sulphate solution typically has a pH in the range of about 5-5.5.

After removal of sildenafil which has not been included by means of gel filtration, both the active ingredient content and the lipid content were determined by means of rp-HPLC. Liposome size and distribution were determined by means of photon correlation spectroscopy (PCS).

Depending on the vesicle size, inclusion rates (represented as sildenafil/lipid ratio) of 160 to 230 nmol of sildenafil per µmol of total lipids (=DPPC+cholesterol) were achievable by this method of active loading. This converts to values of 1000-1500 µg of active ingredient per ml of liposomal suspension.

In order to achieve an increase in the amount of liposomally included sildenafil, the sildenafil content in the glucose solution was increased. However, it was found that an excess of active ingredient could not improve the active ingredient/lipid ratio. The effective loading quantity in the case of active external loading via an $H^+$ gradient therefore appears to be dependent primarily on the gradient and to a lesser extent on the initially taken active ingredient concentration.

b) One-Stage Variant:

The lipids (DPPC:cholesterol=55:45 mol %) were dissolved in ethanol and the solution was injected into a sildenafil/ammonium sulphate solution (pH 3.5-4.5), whereupon, immediately after spontaneous vesicle formation, a 5% glucose solution (pH 7), which comprised further sildenafil citrate, was added for dilution and alkalinization of the reaction mixture, i.e. of the resulting liposome suspension. As a result of the production of this $H^+$ gradient immediately after the vesicle formation, sildenafil is not only included in the liposomes in one step but is also retained there in a stable manner. The amount of sildenafil included liposomally in this manner was likewise in a range of about 160 to 230 nmol of sildenafil per µmol of total lipids (DPPC+cholesterol)—depending on the pH or $H^+$ gradient.

The active ingredients tadalafil and vardenafil were also loaded into liposomes in an analogous manner.

For comparison purposes, liposomally incorporated prostaglandin E1 was also produced under similar process conditions. Regarding the application effects, cf. Example 2.

EXAMPLE 2

Use of Liposomally Incorporated Active Ingredient

A. Sildenafil, Tadalafil, Vardenafil in Liposomes

A formulation of 0.5 mg of the respective substance (calculated as salt-free active ingredient) in liposomes per 1 ml of hydrogel Carbopol 981 NF was chosen as the pharmaceutical composition for use in a human experiment and used by test persons in an application amount of 0.5-1.5 ml per application, sildenafil and vardenafil being used in each case in the form of their acidic salts (sildenafil citrate and vardenafil hydrochloride trihydrate, respectively).

The gel was used by male test persons for external application to the penis and by female test persons by external vaginal and/or clitoral application.

Results:

a) Male:

Only shortly after application of the preparation, i.e. within a few minutes, test persons experienced a pleasant, warm sensation and stronger sexual arousal. This was followed by a faster and stronger erection and substantially longer lasting stiffness of the penis in comparison with the effects usual or customary before, without application of the preparation. Similar effects were achieved with the three active ingredient preparations.

b) Female:

Vaginal/clitoral application of the liposomal active ingredient gel immediately resulted in an effect which brought about increased blood flow, resulting in a pleasant, warm sensation and subsequently increased production of vaginal secretion. In addition, the test persons reported slight contractions of the vaginal muscles (similar to those during orgasm), an enhanced sexual sensation during sexual intercourse and a stronger sensation of orgasm.

The use of the liposomal active ingredient preparation not only results in sexual stimulation and enhancement of desire but also triggers stimulus more rapidly and hence results in orgasm being reached more quickly.

Duration of action after single application: the effect begins immediately after application of the preparation, the sensations described above lasting for up to 3.5 hours. All three preparations showed a clear effect; the test persons did not report any substantial, noticeable difference between the three different active ingredient preparations.

In contrast to the discoveries from Pfizer studies on women (cf. New York Times, 28 Feb. 2004, "Pfizer Gives Up Testing Viagra on Women"), at any rate the liposomal active ingredient preparations according to the invention appear to be clearly effective even in women on external application. They can therefore also be used for the therapeutic treatment of female sexual dysfunction (FSD), such as, for example, for the treatment of female sexual arousal disorder (FSAD).

B. Prostaglandin E1 in Liposomes

Similar effects were described by the female test persons also after application of liposomal prostaglandin E1. The applied dose was 0.1 mg-0.5 mg per 1 ml of gel and thus slightly below the dose of sildenafil, tadalafil and vardenafil.

The invention claimed is:

1. A pharmaceutical composition for topical application that has a relaxing effect on smooth muscles, comprising: unilammellar liposomes having a molar fraction of cholesterol of 0-50%, based on the total amount of lipids in the liposomes, wherein the interior of the liposomes comprises, an aqueous ammonium sulfate buffer having a pH in the range of 5.0-5.5 and protonated sildenafil or vardenafil at a concentration of at least 100 nmol per µmol of lipid, and wherein the liposomes are in an aqueous medium comprising a 5% glucose at a pH of 7 to 8.

2. The pharmaceutical composition of claim 1, wherein the liposomes comprise phospholipids having an acyl chain length of at least 14 carbon atoms.

3. The pharmaceutical composition of claim 2, wherein the acyl chain length is at least 16 carbon atoms.

4. The pharmaceutical composition of claim 1, wherein the liposomes have an average size in the range of 150 to 500 nm.

5. The pharmaceutical composition of claim 1, wherein the liposomes comprise sildenafil or vardenafil at a concentration of 150-400 nmol per µmol of lipid.

6. The pharmaceutical composition of claim 1, wherein the composition is in the form of a gel.

7. The pharmaceutical composition of claim 1, wherein the composition is present in aseptic form.

8. A method of prophylactic or therapeutic treatment of male erectile dysfunction, comprising transdermally or transmucosally administering to the genitals of a subject in need of said treatment, the pharmaceutical composition of claim 1, wherein the composition penetrates the surface and relaxes the smooth muscle underneath to thereby treat the male erectile dysfunction.

9. The method according to claim 8 wherein the pharmaceutical composition is applied externally to a penis.

10. A method of therapeutic treatment of female sexual dysfunction, comprising transdermally or transmucosally administering to the genitals of a subject in need of said treatment the pharmaceutical composition of claim 1, wherein the composition penetrates the surface and relaxes the smooth muscle underneath to thereby treat the female sexual dysfunction.

11. A method of therapeutic treatment of female sexual arousal disorder (FSAD), comprising transdermally or transmucosally administering to the genitals of a subject in need of said treatment the pharmaceutical composition of claim 1, wherein the composition penetrates the surface and relaxes the smooth muscle underneath to thereby treat the FSAD.

12. A method for increasing sexual desire, comprising transdermally or transmucosally administering to the genitals of a subject desiring said increase the pharmaceutical composition of claim 1, wherein said composition penetrates the surface to relax the smooth muscle underneath to thereby increase sexual desire in said individual.

13. The pharmaceutical composition of claim 1, wherein said molar fraction of cholesterol based on the total amount of lipids in the liposomes, is 30-45%.

14. The method of claim 10 or 11, wherein the pharmaceutical composition is applied externally to the vagina, the clitoris, or the combination thereof.

* * * * *

UNITED STATES PATENT AND TRADEMARK OFFICE
CERTIFICATE OF CORRECTION

PATENT NO.       : 8,524,274 B2                                    Page 1 of 1
APPLICATION NO.  : 11/577488
DATED            : September 3, 2013
INVENTOR(S)      : Wagner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1766 days.

Signed and Sealed this
Fifteenth Day of September, 2015

Michelle K. Lee
*Director of the United States Patent and Trademark Office*